United States Patent [19]

Cerri et al.

[11] Patent Number: 5,538,960
[45] Date of Patent: Jul. 23, 1996

[54] HYDRAZONO-5β, 14β-ANDROSTANE DERIVATIVES ACTIVE ON THE CARDIOVASCULAR SYSTEM, AND PHARMACEUTICAL COMPOSITIONS CONTAINING SAME

[75] Inventors: Alberto Cerri, Gessate; Luigi Bernardi; Giuseppe Bianchi, both of Milan; Patrizia Ferrari, Varese; Elena Folpini, Milan; Piero Melloni, Bresso, all of Italy

[73] Assignee: SIGMA-TAU Industrie Farmaceutiche Riunite S.p.A., Rome, Italy

[21] Appl. No.: 106,638

[22] Filed: Aug. 16, 1993

[30] Foreign Application Priority Data

Aug. 20, 1992 [DE] Germany .......................... 42 27 626.8

[51] Int. Cl.$^6$ .......................... C07D 43/00; A61K 31/57
[52] U.S. Cl. .......................... 514/176; 540/108; 540/109
[58] Field of Search ........................ 540/109, 108; 514/176

[56] References Cited

U.S. PATENT DOCUMENTS

| 4,460,509 | 7/1984 | Mosbach et al. | 540/109 |
| 5,380,841 | 1/1995 | McCall et al. | 540/111 |
| 5,444,055 | 8/1995 | Cerri | 540/108 |

OTHER PUBLICATIONS

Chemical abstracts vol. 121:157960 (1994).
Chemical abstracts vol. 121:57780 (1994).

*Primary Examiner*—Nicholas Rizzo
*Attorney, Agent, or Firm*—Oblon, Spivak, McClelland, Maier & Neustadt

[57] ABSTRACT

The present invention relates to new 17-hydrazonomethyl- and 17-hydrazono-14β-hydroxy-5β-androstane derivatives active on the cardiovascular system, to a process for their preparation and to pharmaceutical compositions containing same for the treatment of cardiovascular disorders, such as heart failure and hypertension.

9 Claims, No Drawings

HYDRAZONO-5β, 14β-ANDROSTANE DERIVATIVES ACTIVE ON THE CARDIOVASCULAR SYSTEM, AND PHARMACEUTICAL COMPOSITIONS CONTAINING SAME

SUMMARY OF THE INVENTION

The compounds of the present invention have general formula (I):

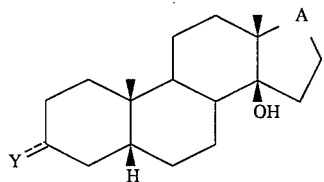
(I)

wherein:

the symbol --- represents a single or a double bond:

A represents

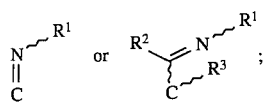

the symbol ⁓⁓⁓ means α or β configuration or a Z or E configuration;

when --- is a single bond Y represents β-$OR^4$:

when --- is a double bond Y represents a N NHC(=N ⁓⁓⁓$R^5$)$NR^6R^7$ group;

$R^1$ represents NHC(=X)T or $NR^6R^7$;

X represents O, S or N ⁓⁓⁓$R^5$;

T represents $NR^6R^7$, NHC(=NH)$NH_2$ or $SR^8$;

provided that when $R^2$ is hydrogen and $R^1$ is NHC(=X)T or $NR^6R^7$, where $R^6$ and $R^7$ are hydrogen, X is oxygen or NH and T is $NH_2$. Y is different from β-OH or $R^3$ is different from hydrogen, and also provided that, when X is oxygen or sulphur, T is not $SR^8$:

$R^2$ represents hydrogen or methyl:

$R^3$ represents hydrogen or hydroxy;

$R^4$ represents hydrogen, C2–C4 alkyl unsubstituted or substituted by $NR^9R^{10}$;

$R^5$ represents hydrogen, methyl, C2–C4 alkyl, C2–C4 acyl or phenyl, where the C2–C4 alkyl, C2–C4 acyl are Unsubstituted or substituted by $NR^9R^{10}$;

$R^6$, $R^7$ which may be the same or different, represent hydrogen, methyl or C2–C4 alkyl unsubstituted or substituted $NR^9R^{10}$;

$R^8$ represents C1–C4 alkyl;

$R^9$, $R^{10}$ which may be the same or different, represent hydrogen, C1–C4 alkyl or $R^9$ and $R^{10}$ may form, taken together with the nitrogen atom, a five- or six-membered monoheterocyclic ring optionally containing other heteroatoms selected from oxygen and nitrogen;

$R^5$, $R^6$, $R^7$ taken two by two may form, together with the heteroatoms they are linked to and where possible, a five- or six- or seven-membered heteromonocyclic ring.

Where the compounds of formula (I) can exhibit tautomerism, the formula is intended to cover all tautomers; the invention encompasses within its scope all the possible stereoisomers, Z and E isomers, optical isomers and their mixtures, the metabolites and the metabolic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as e. g., hydrochloric, hydrobromic, sulfuric, phosphoric, fumaric, succinic, oxalic, malic, tartaric, maleic, citric, methanesulfonic or benzoic acid and others commonly used in the art.

The compounds of the invention also include solvates (e.g. hydrates).

N-oxides, where the nitrogen atom is not substituted with a hydrogen atom, are also encompassed by the invention.

The alkyl groups are branched or straight chain groups or cyclic groups.

The C2–C4 alkyl is preferably ethyl, n-propyl, iso-propyl, n-butyl or tert-butyl.

The C1–C4 alkyl is preferably methyl, ethyl, n-propyl, iso-propyl, n-butyl, tert-butyl.

The C2–C4 acyl is preferably acetyl, propionyl, n-butyryl or iso-butyryl.

The $R^4$ group is preferably hydrogen, 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl.

The $R^5$ group is preferably hydrogen, methyl, 2-aminoethyl, 3-aminopropyl, 2-dimethylaminoethyl, 3-dimethylaminopropyl, 2-(1-pyrrolidinyl)ethyl, 3-(1-pyrrolidinyl)propyl, acetyl, phenyl.

The $NR^6R^7$ group is preferably amino, methylamino, dimethylamino, diethylamino, iso-propylamino, pyrrolidinyl, piperidyl, morfolino, piperazin-1-yl, 4-methylpiperazin-1-yl, 4-(2-hydroxyethyl)piperazin-1-yl, 4-(2-dimethylaminoethyl)piperazin-1-yl, 2-dimethylaminoethylamino, 2-diethylaminoethylamino, (2-dimethylaminoethyl)methylamino, (2-diethylaminoethyl)methylamino, 3-dimethylaminopropylamino, (3-dimethylaminopropyl)methylamino, 2-(1-pyrrolidinyl)ethylamino, 3-(1-pyrrolidinyl)propylamino, (2-(1-pyrrolidinyl)ethyl)methylamino.

The $NR^9R^{10}$ group is preferably amino, methylamino, dimethylamino, ethylamino, diethylamino, iso-propylamino, pyrrolidinyl, morfolino.

$R^5$ and $R^6$ groups taken together with the heteroatom they are linked to, are preferably 2-imidazolin-2-yl, 1-methyl-2-imidazolin-2-yl, 5-oxo-2-imidazolin-2-yl, 1-methyl-5-oxo-2-imidazolin-2-yl, 2-imidazolyl, 2-(1-methyl)imidazolyl, 1,4,5,6-tetrahydro-2-pyrimidinyl, 1-methyl-1,4,5,6-tetrahydro-2-pyrimidinyl, 1,4,5,6-tetrahydro-6-oxo-2-pyrimidinyl or 1-methyl-1,4,5,6-tetrahydro-6-oxo-2-pyrimidinyl.

Preferred examples of specific compounds according to the present invention are (E)-17β-(3-methylguanidino)iminomethyl-5β-androstane-3β,14β-diol (E)-17β-(3,3-dimethylguanidino)iminomethyl-5β-androstane- 3β,14β-diol (E)-17β-(2-imidazolin-2-yl)hydrazonomethyl-5β-androstane- 3β,14β-diol (E)-17β-(2-imidazolyl)hydrazonomethyl-5β-androstane-3β, 14β-diol (E)-17β-(1-methyl-2-imidazolin-2-yl)hydrazonomethyl-5β-androstane- 3β,14β-diol (E)-17β-(5-oxo-2-imidazolin-2-yl)hydrazonomethyl-5β-androstane- 3β,14β-diol (E)-17β-(1,4,5,6-tetrahydro-2-pyrimidinyl)hydrazonomethyl-5β-androstane- 3β,14β-diol (E)-17β-(3-amidino)guanidinoiminomethyl-5β-androstane-3β,14β-diol (E)-17β-(3-(2-dimethylaminoethyl)guanidino)iminomethyl-
   5β-androstane- 3β,14β-diol
(E)-17β-(3-phenylguanidino)iminomethyl-5β-androstane-
   3β,14β-diol
(E)-17β-dimethylhydrazonomethyl-5β-androstane-3β,14β-
   diol
(E)-17β-thiosemicarbazonomethyl-5β-androstane-3β,14β-
   diol
(E)-17β-(3-methylisothiosemicarbazono)methyl-5β-andros-
   tane-3β,14β-diol
(E)-3β-(3-aminopropoxy)-17β-guanidinoiminomethyl-5β-
   androstane- 14β-ol
(E)-3β-(3-aminopropoxy)-17β-semicarbazonomethyl-5β-
   androstane- 14β-ol
(E)-3β-(3-aminopropoxy)-17β-(3-methylguanidino)imi-
   nomethyl-5β-androstane- 14β-ol
(E)-3β-(3-aminopropoxy)-17β-(3,3-dimethylguanidi-
   no)iminomethyl- 5β-androstane-14β-ol
(E)-3β-(3-aminopropoxy)-17β-(2-imidazolin-2-yl)hydra-
   zonomethyl- 5β-androstane-14β-ol
(E)-3β-(3-aminopropoxy)-17β-(2-imidazolyl)hydrazono-
   methyl-5β-androstane- 14β-ol
(E)-3β-(3-aminopropoxy)-17β-(1-methyl-2-imidazolin-2-
   yl)hydrazonomethyl- 5β-androstane-14β-ol
(E)-3β-(3-aminopropoxy)-17β-(5-oxo-2-imidazolin-2-yl-
   )hydrazonomethyl- 5β-androstane-14β-ol
(E)-3β-(3-aminopropoxy)-17β-(1,4,5,6-tetrahydro-2-pyrim-
   idinyl)hydrazonomethyl- 5β-androstane-14β-ol
(E)-3β-(3-aminopropoxy)-17β-(3-amidino)guanidinoimi-
   nomethyl- 5β-androstane-14β-ol
(E)-3β-(3-aminopropoxy)-17β-(3-(2-dimethylaminoeth-
   yl)guanidino)iminomethyl- 5β-androstane-14β-ol
(E)-3β-(3-aminopropoxy)-17β-(3-phenylguanidino)imi-
   nomethyl-5β-androstane- 14β-ol
(E)-3β-(3-aminopropoxy)-17β-dimethylhydrazonomethyl-
   5β-androstane- 14β-ol
(E)-3β-(3-aminopropoxy)-17β-thiosemicarbazonomethyl-
   5β-androstane- 14β-ol
(E)-3β-(3-aminopropoxy)-17β-(3-methylisothiosemicarba-
   zono)methyl- 5β-androstane-14β-ol
3-((Z,E)-guanidinoimino)-17β-((E)-guanidinoiminom-
   ethyl))-5β-androstane- 14β-ol
3-((Z,E)-(2-imidazolin-2-yl)hydrazono)-17β-((E)-(2-imida-
   zolin-2 -yl)hydrazono)methyl-5β-androstane-14β-ol
(E)-20-guanidinoimino-5β-pregnane-3β,14β-diol
(E)-20-(2-imidazolin-2-yl)hydrazono-5β-pregnane-3β,14β-
   diol
(E)-3β-(3-aminopropoxy)-20-guanidinoimino-5β-preg-
   nane-14β-ol
(E)-3β-(3-aminopropoxy)-20-(2-imidazolin-2-ylhydra-
   zono)-5β-pregnane- 14β-ol
(E)-17β-guanidinoiminomethyl-5β-androstane-3β,14β,
   17α-triol
(E)-17β-semicarbazonomethyl-5β-androstane-3β,14β,17α-
   triol
(E)-17β-(3-methylguanidino)iminomethyl-5β-androstane-
   3β,14β,17α-triol
(E)-17β-(3,3-dimethylguanidino)iminomethyl-5β-andros-
   tane- 3β,14β,17α-triol
(E)-17β-(2-imidazolin-2-yl)hydrazonomethyl-5β-andros-
   tane- 3β,14β,17α-triol
(E)-17β-(2-imidazolyl)hydrazonomethyl-5β-androstane-
   3β,14β,17α-triol
(E)-17β-(1-methyl-2-imidazolin-2-yl)hydrazonomethyl-5β-
   androstane- 3β,14β,17α-triol
(E)-17β-(5-oxo-2-imidazolin-2-yl)hydrazonomethyl-5β-an-
   drostane- 3β,14β,17α-triol
(E)-17β-(1,4,5,6-tetrahydro-2-pyrimidinyl)hydrazonom-
   ethyl-5β-androstane- 3β,14β,17α-triol
(E)-17β-(3-amidino)guanidinoiminomethyl-5β-androstane-
   3β,14β,17α-triol
(E)-17β-(3-(2-dimethylaminoethyl)guanidino)iminomethyl-
   5β-androstane- 3β,14β,17α-triol
(E)-17β-(3-phenylguanidino)iminomethyl-5β-androstane-
   3β,14β,17α-triol
(E)-17β-dimethylhydrazonomethyl-5β-androstane-3β,14β,
   17α-triol
(E)-17β-thiosemicarbazonomethyl-5β-androstane-3β,14β,
   17α-triol
(E)-17β-(3-methylisothiosemicarbazono)methyl-5β-andros-
   tane- 3β,14β,17β-triol
(E)-3β-(3-aminopropoxy)-17β-guanidinoiminomethyl-5β-
   androstane- 14β,17α-diol
(E)-3β-(3-aminopropoxy)-17β-semicarbazonomethyl-5β-
   androstane- 14β,17α-diol
(E)-3β-(3-aminopropoxy)-17β-(3-methylguanidino)imi-
   nomethyl-5β-androstane- 14β,17α-diol
(E)-3β-(3-aminopropoxy)-17β-(3,3-dimethylguanidi-
   no)iminomethyl- 5β-androstane-14β,17α-diol
(E)-3β-(3-aminopropoxy)-17β-(2-imidazolin-2-yl)hydra-
   zonomethyl- 5β-androstane-14β,17α-diol
(E)-3β-(3-aminopropoxy)-17β-(2-imidazolyl)hydrazonom-
   ethyl-5β-androstane- 14β,17α-diol
(E)-3β-(3-aminopropoxy)-17β-(1-methyl-2-imidazolin-2-
   yl)hydrazonomethyl- 5β-androstane-14β,17α-diol
(E)-3β-(3-aminopropoxy)-17β-(5-oxo-2-imidazolin-2-yl)
   hydrazonomethyl- 5β-androstane-14β,17α-diol
(E)-3β-(3-aminopropoxy)-17β-(1,4,5,6-tetrahydro-2-pyrim-
   idinyl)hydrazonomethyl- 5β-androstane-14β,17α-diol
(E)-3β-(3-aminopropoxy)-17β-(3-amidino)guanidinoimi-
   nomethyl- 5β-androstane-14β,17α-diol
(E)-3β-(3-aminopropoxy)-17β-(3-(2-dimethylaminoeth-
   yl)guanidino)iminomethyl- 5β-androstane-14β,17α-diol
(E)-3β-(3-aminopropoxy)-17β-(3-phenylguanidino)imi-
   nomethyl- 5β-androstane- 14β,17α-diol
(E)-3β-(3-aminopropoxy)-17β-dimethylhydrazonomethyl-
   5β-androstane-14β,17α-diol
(E)-3β-(3-aminopropoxy)-17β-thiosemicarbazonomethyl-
   5β-androstane- 14β,17α-triol
(E)-3β-(3-aminopropoxy)-17β-(3-methylisothiosemicarba-
   zono)methyl- 5β-androstane-14β,17α-diol
3-((Z,E)-guanidinoimino)-17β-((E)-guanidinoimino)m-
   ethyl-5β-androstane- 14β,17α-diol
3-((Z,E)-(2-imidazolin-2-yl)hydrazono)-17β-((E)-(2-imida-
   zolin-2 -yl)hydrazono)methyl-5β-androstane-14β,17α-
   diol
(E)-20-guanidinoimino-5β-pregnane-3β,14β,17α-triol
(E)-20-((2-imidazolin-2-yl)hydrazono)-5β-pregnane-3β,
   14β,17α-triol
(E)-3β-(3-aminopropoxy)-20-guanidinoimino-5β-preg-
   nane- 14β,17α-diol
(E)-3β-(3-aminopropoxy)-20-((2-imidazolin-2-yl)hydra-
   zono)-5β-pregnane- 14β,17α-diol
(E)-3β-(3-aminopropoxy)-17-guanidinoimino-5β-andros-
   tane-14β-ol
(E)-17-(2-imidazolin-2-yl)hydrazono-5β-androstane-3β,
   14β-diol
(E)-3β-(3-aminopropoxy)-17-(2-imidazolin-2-yl)hydra-
   zono-5β-androstane- 14β-ol
and where there are the (E) isomers also the correspond-
ing (Z) isomers;
and where there are the 3β-(3-aminopropoxy) substituents
also the corresponding 3β-(3-dimethylaminopropoxy),
3β-(3-diethylaminopropoxy), 3β-(3-(1-pyrrolidinyl)pro-
poxy), 3β-(2-aminoethoxy), 3β-(2 -dimethylaminoethoxy),
3β-(2-diethylaminoethoxy) and 3β-(2-(1 -pyrrolidi-
nyl)ethoxy) compounds.

17-Guanidinoiminomethyl-5β-androstane-3β,14β-diol and 17-guanidinoimino-5β-androstane-3β,14β-diol are reported to be weak inhibitors of Na+,K+-ATPase and weak positive inotropic agents (Gelbart A. and Thomas R., *J. Med. Chem.*, 1978, 21, 284; Schönfeld W. and Repke K., *Quant. Struct.-Act. Relat.*, 1988, 7, 160). Other 20-substituted hydrazonomethyl-5β-androstane-3β,14β-diols (20-ureidoimino, 20-hydrazono) are reported not to inhibit Na+,K+-ATPase (Thomas R. et al., *J. Pharmacol. Exp. Ther.*, 1974, 191, 219; Boutagy J. et al., *Aust. J. Pharm. Sci.*, 1973, 2, 41).

The invention furthermore provides a process for the preparation of compounds of general formula I, which comprises a condensation reaction of compounds of formula II

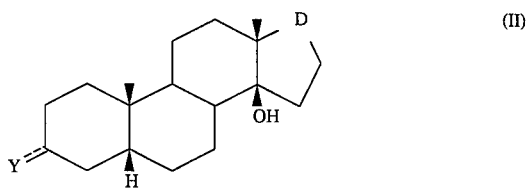

(II)

in which: Y and the symbol --- are as above defined and D has the following meanings:

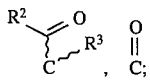

where R² and R³ are as above defined, with a compound of general formula III and IV

H₂NNHC(=X)T    (III)

H₂NNR⁶R⁷    (IV)

to give compounds of general formula I where R¹ is as above defined. Compounds (III) and (IV) can be used as the free base or in the form of a salt with an acid such as, e.g., hydrochloric, carbonic, oxalic, hydriodic or sulfuric acid. The reaction can be carried out in a solvent, such as ethanol, methanol, acetonitrile, dioxane, tetrahydrofuran, water or a mixture of said solvents, at a temperature between 0° C. and the boiling point of the above mentioned solvents or of their mixtures. To the reaction mixtures, additional salts, such as, e.g., NaH₂PO₄, Na₂HPO₄, NaOAc, can be added as well as acids such as, e.g., hydrochloric, sulfuric, acetic, phosphoric acid, and bases such as, e.g., sodium or potassium hydroxide, to maintain the desired pH.

The groups optionally present in Y and/or R² and/or R³ are protected, if necessary, by known methods, to give after removal by known methods of protective groups, if any, compounds of general formula (I) which can be converted into other compounds of general formula (I) by known methods.

Compounds of general formula (II)

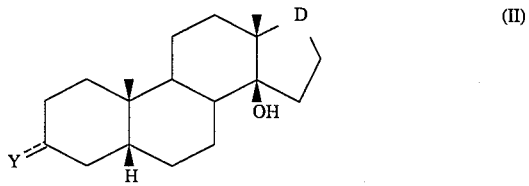

(II)

in which: Y and the symbol --- are as above defined and D has the following meanings:

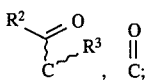

where R² and R³ are as above defined and Y is oxygen, when --- is a double bond, or 3β-hydroxy, when --- is a single bond, are known compounds (Lindig C., *J. Prakt. Chem.*, 1983, 325, 587; Boutagy J. and Thomas R., *Aust. J. Chem.*, 1971, 24, 2723;, *Aust. J. Pharm. Sci.*, (NS), 1973, 2, 9; Templeton J. F. et al., *J. Med. Chem.*, 1989, 32, 1977; Templeton J. F. et al., *J. Chem. Soc., Perkin Trans.* 1, 1991, 823; Danieli N. et al., *Tetrahedron*, 1967, 23, 715) or are prepared from the known compounds with methods well known to those skilled in the art.

For example the unknown 3β-hydroxy compounds are prepared from the corresponding known 3-keto compounds by reduction with Li-selectride.

Conversely, when the 3β-hydroxy is a known compound the corresponding unknown 3-keto compound is obtained by oxidation with known methods such as Jones reagent, chromic anhydride in pyridine or tetrapropylammonium perruthenate and N-methylmorpholine N-oxide.

When the 17α-hydroxy-20-carbonyl compounds are unknown compounds they are obtained from the corresponding 17α-hydrogen-20-carbonyl compounds by careful oxidation with selenium dioxide e.g. in dioxane in the presence of a base, such as pyridine or triethylamine, at a temperature ranging from 20° C. to the boiling point of the solvent.

Unknown 17α-pregnanes and 17α-formylandrostanes derivatives are prepared from the corresponding 20-oxo-17-epimeric compounds unsubstituted in position 17α by isomerization in alkaline conditions. The introduction of the hydroxy group in position 17β is performed with the methods described above for the corresponding 17 epimers.

Compounds (II) where --- is a double bond and Y is N NHC(=N~~R⁵)NR⁶R⁷ are obtained from compounds (II) where Y is oxygen and --- is a double bond by reaction with a compound of formula (V)

H₂NNHC(=N~R⁵)NR⁶R⁷    (V)

Compounds (II) where --- is a single bond and Y is OR⁴, where R⁴ is different from hydrogen, are prepared from the corresponding compounds (II) where Y is 3β-hydroxy by reaction with a compound of formula (VI)

R⁴W    (VI)

where R⁴ is different from hydrogen and W is an electron-withdrawing group, such as halogen, mesyloxy, or tosyloxy group, which confers electrophilic properties to the attached carbon atom, and R⁴ is as above defined. The reaction is best carried out in an inert aprotic solvent, such as tetrahydrofuran, dioxane, dimethylformamide, dimethylsulfoxyde or in neat R⁴W and in the presence of a base, e.g. sodium or potassium hydride, at a temperature ranging from 0° C. to 110° C.

The groups optionally present in Y and/or R² and/or R³ are protected, if necessary, by known methods to give, after removal by known methods of protective groups, if any, possibly present in Y and/or R² and/or R³, a compound of general formula (II).

Compounds of general formula (III), (IV), (V) and (VI) are known compounds, generally commercially available or preparable from known compounds by known methods.

Compounds of general formula (I) prepared according to the invention and their pharmaceutically acceptable salts are useful agents for the treatment of cardiovascular disorders such as heart failure and hypertension.

Compounds of general formula (I) prepared according to the invention and their pharmaceutically acceptable salts have highly reduced toxicity compared to known positive inotropic agents such as ouabain and digitoxin.

Moreover said compounds (I) show good affinity for the receptor site of the $Na^+,K_+$-ATPase and behave as partial agonists on the enzimatic activity of the $Na^+,K_+$-ATPase.

To test the affinity for the receptor site of the $Na^+,K_+$-ATPase and the agonist or antagonist activity on the enzyme, the following tests were used:

a) displacement of the specific $^3$H-ouabain binding from the $Na^+,K_+$-ATPase receptor purified according to Jorghensen (Jorghensen P., BBA, 1974, 356, 36) and Erdmann (Erdmann E. et al., Arzneim. Forsh., 1984, 34, 1314);

b) inhibition of the activity of the purified $Na^+,K_+$-ATPase measured as % of hydrolysis of $^{32}$P-ATP in presence and in absence of the tested compound (Mall F. et al., Biochem. Pharmacol, 1984, 33, 47)

Systolic blood pressure (SBP) and heart rate (HR) were measured, by the tail cuff method, in young prehypertensive male rats (MHS or SHR) strains before the development of hypertension (4 weeks of age) for recording the basal values of SBP. Groups of 7 rats were formed and subdivided in control and treated groups. The compound, suspended in Methocel 0.5 % (w/v), was orally given daily for at least 5 weeks to the treated groups. The control group received only Methocel.

SBP and HR were measured weekly 6 and 24 hrs after treatment. After 5 weeks of treatment, when hypertension was fully developed in the control group (9 weeks of age), washout was started for at least one week, to verify whether the treatment mantained blood pressure low or reestablished the basal values. The validity of this procedure for detecting an hypotensive activity, had been previously tested for β blockers, which did not produce any hypotensive effect when acutely given to hypertensive rats (SHR), but were effective in preventing the development of hypertension when administered starting from weaning for more than 5 weeks. (Takeda K. et al., Japan J. Pharmacol, 1979, 29,171; Takeda K. et al. Japan J. Pharmacol., 1982, 32, 283; Richer C. et al. Eur. J. Pharmacol, 1978, 47,393).

The affinity and the inhibitory activity of some compounds in the two tests are shown in the following table:

| | Binding $^3$H-Ouab. Displacement -log IC50 | Inhibitory Activity -log IC50 |
| --- | --- | --- |
| Comp. I-aa | 6.7 | 5.2 |
| Comp. I-ac | 6.0 | 4.9 |
| Comp. I-ad | 5.0 | 4.0 |
| Comp. I-ae | 6.6 | 5.3 |
| Comp. I-af | 6.7 | 5.1 |
| Comp. I-ag | 6.0 | 4.6 |
| Comp. I-ah | 5.2 | 4.0 |
| Comp. I-ai | 5.0 | 4.0 |
| Comp. I-aj | 5.0 | 4.0 |
| Comp. I-ak | 5.7 | 4.5 |
| Comp. I-al | 7.4 | 6.1 |
| Comp. I-an | 7.4 | 6.3 |
| Comp. I-aq | 5.9 | 4.4 |
| Comp. I-as | 5.8 | 4.4 |
| Comp. I-au | 7.0 | 5.4 |
| Comp. I-aw | 7.0 | 6.4 |
| Comp. I-bi | 6.9 | 5.3 |
| Comp. I-bk | 6.6 | 5.3 |
| Comp. I-bl | 5.8 | 4.4 |
| Comp. I-bn | 5.4 | 4.9 |
| Comp. I-bo | 5.7 | 4.4 |

The activity of some new compound in preventing the development of hypertension is shown in the following table:

EFFECT OF 5 WEEK-TREATMENT IN SPONTANEOUS HYPERTENSIVE RATS (MHS) ON THE DEVELOPMENT OF HYPERTENSION

| Compound | RATS | DOSE* mg/Kg/os | SBP mm Hg | HR beats/min. |
| --- | --- | --- | --- | --- |
| Controls | 7 | Methocel | 172 +/− 3.5 | 380 +/− 9.0 |
| Comp. I-aa | 7 | 20 | 149 +/− 3.7 | 370 +/− 11.2 |
| Comp. I-ag | 7 | 20 | 154 +/− 4.8 | 390 +/− 5.9 |
| Comp. I-al | 7 | 20 | 153 +/− 6.3 | 380 +/− 10.0 |
| Comp. I-an | 7 | 20 | 150 +/− 5.1 | 384 +/− 7.9 |
| Comp. I-aw | 7 | 20 | 151 +/− 5.2 | 388 +/− 9.0 |

*in Methocel 0.5% w/v

The following examples illustrate the invention without limiting it.

EXAMPLE 1

(E)-17β-(2-Imidazolin-2-yl)hydrazonomethyl-5β-androstane- 3β,14β-diol (I-aa)

To a solution of 0.93 g of 2-hydrazino-2-imidazoline hydrobromide in 45 ml of water and 30 ml of dioxane a solution of 1.10 g of 3β,14β-dihydroxy-5β-androstane-17β-carboxaldehyde (Boutagy J. and Thomas R., Aust. J. Chem., 1971, 24, 2723) in 30 ml of dioxane was added dropwise at room temperature. After 2 hrs, the solution was evaporated to dryness under reduced pressure. The crude product was crystallized from ethanol/water and then from ethanol to give 0.60 g of the title compound (I-aa) as hydrobromide, white solid.

$^1$H-NMR (300 MHz, DMSO-$d_6$, ppm from TMS): 0.78 (3H, s); 0.87 (3H, s); 2.20–2.35 (1H, m); 3.60 (4H, s); 3.88 (1H, m); 4.17 (1H, s); 4.21 (1H, d); 7.63 (1H, d); 7.70–8.80 (2H, bb); 11.80 (1H, bb).

EXAMPLE 2

(E)-17β-(2-Imidazolyl)hydrazonomethyl-5β-androstane-3β,14β-diol (I-ab)

The title compound (I-ab) (0.42 g) was obtained as a white solid starting from 3β,14β-dihydroxy-5β-androstane-17β-carboxaldehyde (0.95 g) (Boutagy J. and Thomas R., Aust. J. Chem., 1971, 24, 2723) and 2-hydrazinoimidazole (prepared from 2-methylthioimidazole and hydrazine following the procedure described in Houben-Weil, Metoden der Organischen Chemie, Band VIII, page 183) using the same procedure described in Ex. 1.

$^1$H-NMR (300 MHz, DMSO-$d_6$, ppm from TMS): 0.79 (3H, s); 0.88 (3H, s); 2.20–2.35 (1H, m); 3.89 (1H, m); 4.10 (1H, s); 4.20 (1H, d); 6.87 (2H, s).

EXAMPLE 3

(E)-17β-(1-Methyl-2-imidazolin-2-yl)
hydrazono-methyl-5β-androstane- 3β,14β-diol (I-ac)

The title compound (I-ac) (0.33 g) was obtained as hydroiodide, white solid, starting from 3β,14β-dihydroxy-5β-androstane-17β-carboxaldehyde (0.80 g) (Boutagy J. and Thomas R., *Aust. J. Chem.*, 1971, 2 4, 2723) and 1-methyl-2-hydrazinoimidazoline hydroiodide (prepared from 2-methylthio-1-methylimidazoline hydroiodide and hydrazine following the procedure described in Houben-Weil, Metoden der Organischen Chemie, Band VIII, page 183) using the same procedure described in Ex. 1.

$^1$H-NMR (300 MHz, DMSO-$d_6$, ppm from TMS): 0.79 (3H, s); 0.88 (3H, s); 2.20–2.35 (1H, m); 3.10 (3H, s); 3.63 (4H, s); 3.88 (1H, m); 4.15 (1H, s); 4.20 (1H, d); 7.64 (1H, d); 7.70–8.70 (1H, bb); 11.60 (1H, bb).

EXAMPLE 4

(E)-17β-(5-Oxo-2-imidazolin-2-yl)
hydrazonomethyl-5β-androstane- 3β,14β-diol (I-ad)

The title compound (I-ad) (0.41 g) was obtained as free base, white solid, starting from 3β,14β-dihydroxy-5β-androstane-17β-carboxaldehyde (0.90 g) (Boutagy J. and Thomas R., *Aust. J. Chem.*, 1971, 2 4, 2723) and 5-oxo-2-hydrazinoimidazoline hydroiodide (prepared from 2-methylthio-5-oxo-2-imidazoline hydroiodide and hydrazine following the procedure described in Houben-Weil, Metoden der Organischen Chemie, Band VIII, page 183) using the same procedure described in Ex. 1.

$^1$H-NMR (300 MHz, DMSO-$d_6$, ppm from TMS): 0.79 (3H, s); 0.87 (3H, s); 2.30–2.40 (1H, m); 3.72 (1H, d); 3.87 (1H, m); 3.90 (1H, s); 3.95 (1H, d); 4.17 (1H, d); 7.08 (1H, d); 7.40 (1H, b); 8.10 (1H, b).

EXAMPLE 5

(E)-17β-(1,4,5,6-Tetrahydro-
2-pyrimidinyl)hydrazonomethyl-
5β-androstane-3β,14β-diol (I-ae)

The title compound (I-ae) (0.33 g) was obtained as hydroiodide, white solid, starting from 3β,14β-dihydroxy-5β-androstane-17β-carboxaldehyde (0.90 g) (Boutagy J. and Thomas R., *Aust. J. Chem.*, 1971, 2 4, 2723) and 2-hydrazino-1,4,5,6-tetrahydro-2-pyrimidine hydroiodide (prepared from 2-methylthio-1,4,5,6-tetrahydro-2-pyrimidine hydroiodide and hydrazine following the procedure described in Houben-Weil, Metoden der Organischen Chemie, Band VIII, page 183) using the same procedure described in Ex. 1.

$^1$H-NMR (300 MHz, DMSO-$d_6$, ppm from TMS): 0.76 (3H, s); 0.87 (3H, s); 2.25–2.35 (1H, m); 3.25 (4H, m); 3.88 (1H, m); 4.15 (1H, s); 4.20 (1H, d); 7.57 (1H, d); 7.90 (2H, bb); 11.10 (1H, bb).

EXAMPLE 6

(E)-17β-(3-Amidino)guanidinoiminomethyl-
5β-androstane- 3β,14β-diol (I-af)

To a solution of 0.41 g of sodium ethoxide in 10 ml of anhydrous ethanol 0.57 g of guanidine hydrochloride and 0.90 g of (E)-17β-(3-methylisothiosemicarbazono)methyl-5β-androstane-3β,14β-diol (I-ak) were added in the order at room temperature. After 4 hrs at reflux the solution was cooled and evaporated to dryness under reduced pressure. The residue was purified by flash-chromatography (SiO$_2$) using chloroform/methanol/28% ammonium hydroxide 77/20/3 as eluant; the fractions containing the title compound were collected and evaporated to dryness. The residue was ground with ethanol to give 0.20 g of the title compound (I-af) as a white solid.

$^1$H-NMR (300 MHz, DMSO-$d_6$, ppm from TMS): 0.76 (3H, s); 0.89 (3H, s); 2.25 (1H, m); 3.88 (1H, m); 3.98 (1H, s); 4.15 (1H, d); 4.50–6.50 (6H, bb); 7.45 (1H, d).

EXAMPLE 7

(E)-17β-(3-(2-Dimethylaminoethyl)guanidinoimino)
methyl-5β-androstane- 3β,14β-diol (I-ag)

To a solution of 0.64 g of 1-amino-3-(2-dimethylaminoethyl)guanidine hydroiodide (prepared following the procedure described in Houben-Weil, Metoden der Organischen Chemie, Band VIII, page 183) in 20 ml of $10^{-4}$M hydrochloric acid a solution of 1.10 g of 3β,14β-dihydroxy-5β-androstane-17β-carboxaldehyde (Boutagy J. and Thomas R., *Aust. J. Chem.*, 1971, 24, 2723) in 25 ml of dioxane was added dropwise at room temperature. After 3 hrs, the solution was evaporated to dryness under reduced pressure. The crude product was purified by flash-chromatography (SiO$_2$) using chloroform/methanol/28% ammonium hydroxide 78/20/2 as eluant; the fractions containing the title compound were collected and evaporated to dryness. The residue was ground with di-iso-propyl ether to give 0.15 g of the title compound (I-ag) as hydroiodide, white solid.

$^1$H-NMR (300 MHz, DMSO-$d_6$, ppm from TMS): 0.78 (3H, s); 0.87 (3H, s); 2.19 (6H, s); 2.25–2.35 (1H, m); 2.40 (2H, t); 3.25 (2H, t); 3.88 (1H, m); 4.12 (1H, s); 4.19 (1H, m); 6.70–7.80 (3H, bb); 7.59 (1H, d); 11.50 (1H, bb).

EXAMPLE 8

(E)-17β-(3-Phenylguanidino)iminomethyl-
5β-androstane- 3β,14β-diol (I-ah)

To a solution of 0.83 g of 3-phenyl-1-aminoguanidine hydroiodide (prepared following the procedure described in Houben-Weil, Metoden der Organischen Chemie, Band VIII, page 183) in 10 ml of water and 5 ml of dioxane a solution of 0.64 g of 3β,14β-dihydroxy-5β-androstane- 17β-carboxaldehyde (Boutagy J. and Thomas R., *Aust. J. Chem.*, 1971, 24, 2723) in 5 ml of dioxane was added dropwise at room temperature. After 2 hrs, the solution was evaporated to dryness under reduced pressure. The crude product was purified by flash-chromatography (SiO$_2$) using chloroform/methanol/28% ammonium hydroxide 89/10/1 as eluant; the fractions containing the title compound were collected and evaporated to dryness. The residue was ground with ethanol to give 0.20 g of the title compound (I-ah) as a white solid.

$^1$H-NMR (300 MHz, DMSO-$d_6$, ppm from TMS): 0.82 (3H, s); 0.90 (3H, s); 2.33 (1H, m); 3.88 (1H, m); 3.96 (1H, s); 4.18 (1H, d); 5.53 (2H, bb); 6.82 (1H, m); 7.20 (2H, m); 7.50 (2H, m); 7.63 (1H, d); 8.03 (1H, bb).

EXAMPLE 9

(E)-17β-Dimethylhydrazonomethyl-
5β-androstane-3β,14β-diol (I-ai)

To a solution of 0.80 g of NaH$_2$PO$_4$.H$_2$O, 1.70 g of Na$_2$HPO$_4$.12H$_2$O and 0.12 ml of N,N-dimethylhydrazine in 200 ml of water a solution of 0.64 g of 3β,14β-dihydroxy- 5β-androstane-17β-carboxaldehyde (Boutagy J. and Thomas R., *Aust. J. Chem.*, 1971, 24, 2723) in 20 ml of dioxane was added dropwise at room temperature. After 1.5 hrs the solution was alkalinized with an acqueous solution of NaHCO$_3$ and extracted with ethyl acetate; the organic layer was dried over anhydrous sodium sulfate and evaporated to dryness. The crude product was purified by flash-chromatography (SiO$_2$) using cyclohexane/chloroform/acetone 4/3/3 as eluant to give 0.37 g of the title compound (I-ai), as a white foam.

$^1$H-NMR (300 MHz, DMSO-d$_6$, ppm from TMS): 0.73 (3H, s); 0.87 (3H, s); 2.15–2.25 (1H, m); 2.54 (6H, s); 3.87 (1H, m); 3.92 (1H, s); 4.18 (1H, d); 6.74 (1H, d).

EXAMPLE 10

(E)-17β-Thiosemicarbazonomethyl-5β-androstane-3β,14β-diol (I-aj)

To a solution of 0.43 g of thiosemicarbazide in 20 ml of water a solution of 1.00 g of 3β,14β-dihydroxy-5β-androstane-17β-carboxaldehyde (Boutagy J. and Thomas R., *Aust. J. Chem*, 1971, 24, 2723) in 25 ml of dioxane was added dropwise at room temperature. After 1 hr the solution was diluted with water and extracted with chloroform; the organic layer was dried over anhydrous sodium sulfate and evaporated to dryness. The crude product was purified by flash-chromatography (SiO$_2$) using chloroform/methanol 95/5; the fractions containing the title compound were collected and evaporated to dryness. The residue was crystallized from ethyl acetate/n-hexane to give 0.40 g of the title compound (I-aj), as a white solid.

$^1$H-NMR (300 MHz, DMSO-d$_6$, ppm from TMS): 0.78 (3H, s); 0.88 (3H, s); 2.15–2.30 (1H, m); 3.88 (1H, m); 4.07 (1H, s); 4.20 (1H, d); 7.38 (1H, bs); 7.52 (1H, d); 7.85 (2H, bs); 11.0 (1H, s).

EXAMPLE 11

(E)-17β-(3-Methylisothiosemicarbazono)methyl-5β-androstane- 3β,14-diol (I-ak)

To a solution of 0.22 g of S-methylisothiosemicarbazide hydroiodide in 1.5 ml of water a solution of 200 mg of 3β,14β-dihydroxy- 5β-androstane-17β-carboxaldehyde (Boutagy J. and Thomas R., *Aust. J. Chem.*, 1971, 24, 2723) in 12 ml of dioxane was added dropwise at room temperature. After 30 minutes the solution was evaporated to dryness; the crude product was ground with water to give 0.24 g of the title compound as hydroiodide (I-ak), white solid.

$^1$H-NMR (300 MHz, CD$_3$OD, ppm from TMS): 0.92 (3H, s); 0.98 (3H, s); 2.47–2.60 (1H, m); 2.72 (3H, s); 4.07 (1H, m); 7.87 (1H, d).

EXAMPLE 12

(E)-3β-(3-Aminopropoxy)-17β-guanidinoiminomethyl-5β-androstane- 14β-ol (I-al)

To a solution of 1.00 g 3β-(3-aminopropoxy)-17β-(2-(1,3 -dioxolanyl))-5β-androstane-14β-ol (Prepn. 1), 1.50 g of aminoguanidine hydrogencarbonate and 30 ml of 0.01M hydrochloric acid in 80 ml of dioxane was mantained at room temperature for 3 days. The solution was evaporated to dryness under reduced pressure. The crude product was purified by flash-chromatography (SiO$_2$) using chloroform/methanol/28% ammonium hydroxide 78/20/2 as eluant; the fractions containing the title compound were collected and evaporated to dryness. The residue was crystallized from ethanol/ethyl acetate to give 0.30 g of the title compound (I-al) as a white solid.

$^1$H-NMR (300 MHz, DMSO-d$_6$, ppm from TMS): 0.76 (3H, s); 0.85 (3H, s); 2.20–2.32 (1H, m); 2.56 (2H, t); 3.34 (2H, m); 3.52 (1H, m); 3.92 (1H, s); 5.20–6.10 (4H, bb); 7.43 (1H, d).

EXAMPLE 13

(E)-3β-(2-Aminoethoxy)-17β-guanidinoiminomethyl-5β-androstane- 14β-ol (I-am)

The title compound (I-am) (0.33 g) was obtained as a white solid starting from 3β-(2-aminoethoxy)-17β-(2-(1,3-dioxolanyl))-5β-androstane- 14β-ol (0.75 g) (Prepn. 2) and aminoguanidine hydrogencarbonate using the same procedure described in Ex. 12.

$^1$H-NMR (300 MHz, DMSO-d$_6$, ppm from TMS): 0.76 (3H, s); 0.86 (3H, s); 2.20–2.30 (1H, m); 2.60 (2H, t); 3.40 (2H, m); 3.60 (1H, m); 3.95 (1H, s); 5.00–6.00 (4H, bb); 7.42 (1H, d).

EXAMPLE 14

(E)-3β-(2-(1-pyrrolidinyl)ethoxy)-17β-guanidinoiminomethyl- 5β-androstane-14β-ol (I-an)

To a solution of 1.00 g 3β-(2-(1-pyrrolidinyl)ethoxy)-17β-(2-(1,3 -dioxolanyl))-5β-androstane-14β-ol (Prepn. 3) and 30 ml of 0.1M hydrochloric acid in 80 ml of dioxane was mantained at room temperature for 1 day. After the pH was raised to 5.0 by adding 0.1M sodium hydroxide, 0.30 g of aminoguanidine hydrogencarbonate were added. After 2 days the solution was evaporated to dryness under reduced pressure. The crude product was purified by flash-chromatography (SiO$_2$) using chloroform/methanol/28% ammonium hydroxide 78/20/2 as eluant; the fractions containing the title compound were collected and evaporated to dryness. The residue was crystallized from ethanol/ethyl acetate to give 0.25 g of the title compound (I-an) as a white solid.

$^1$H-NMR (300 MHz, DMSO-d$_6$, ppm from TMS): 0.76 (3H, s); 0.85 (3H, s); 2.20–2.32 (1H, m); 2.45 (4H, m); 2.52 (2H, t); 3.38 (2H, m); 3.54 (1H, m); 3.95 (1H, s); 5.20–6.10 (4H, bb); 7.43 (1H, d).

EXAMPLE 15

(Z)-3β-(2-(1-Pyrrolidinyl)ethoxy)-17β-guanidinoiminomethyl- 5β-androstane-14β-ol (I-ao)

The title compound (I-ao) (0.08 g) was isolated from the reaction described in Ex. 14.

$^1$H-NMR (300 MHz, CD$_3$OD, ppm from TMS): 0.87 (3H, s); 0.89 (3H, s); 2.87 (1H, m); 7.05 (1H, d).

EXAMPLE 16

(E)-3β-(3-(1-Pyrrolidinyl)propoxy)-17β-guanidinoiminomethyl- 5β-androstane-14β-ol (I-ap)

The title compound (I-ap) (0.38 g) was obtained as a white solid starting from 3β-(3-(1-pyrrolidinyl)propoxy)-17β-(2-(1,3-dioxolanyl))-5β-androstane- 14β-ol (0.80 g) (Prepn. 4) and aminoguanidine hydrogencarbonate following the procedure described in Ex. 14.

¹H-NMR (300 MHz, DMSO-d₆, ppm from TMS): 0.76 (3H, s); 0.85 (3H, s); 2.20–2.30 (1H, m); 2.45 (6H, m); 3.30 (2H, m); 3.52 (1H, m); 3.90 (1H, s); 5.30–6.30 (4H, bb); 7.41 (1H, d).

EXAMPLE 17

(E)-3β-(3-Aminopropoxy)-17β-semicarbazonomethyl-5β-androstane-14β-ol (I-aq)

The title compound (I-aq) (0.42 g) was obtained as a white solid starting from 3β-(3-aminopropoxy)-17β-(2-(1,3-dioxolanyl))-5β-androstane- 14β-ol (0.90 g) (Prepn. 1) and semicarbazide hydrochloride using the same procedure described in Ex. 12.

¹H-NMR (300 MHz, DMSO-d₆, ppm from TMS): 0.77 (3H, s); 0.86 (3H, s); 2.19 (1H, m); 2.56 (2H, t); 3.35 (2H, m); 3.53 (1H, m); 3.91 (1H, s); 5.95 (2H, bb); 7.25 (1H, d); 9.63 (1H, s).

EXAMPLE 18

(E)-3β-(2-Aminoethoxy)-17β-semicarbazonomethyl-5β-androstane- 14β-ol (I-ar)

The title compound (I-ar) (0.36 g) was obtained as a white solid starting from 3β-(2-aminoethoxy)-17β-(2-(1,3-dioxolanyl))-5β-androstane- 14β-ol (0.75 g) (Prepn. 2) and semicarbazide hydrochloride using the same procedure described in Ex. 12.

¹H-NMR (300 MHz, DMSO-d₆, ppm from TMS): 0.75 (3H, s); 0.86 (3H, s); 2.20 (1H, m); 2.60 (2H, t); 3.40 (2H, m); 3.60 (1H, m); 3.95 (1H, s); 6.00 (2H, bb); 7.25 (1H, d); 9.65 (1H, s).

EXAMPLE 19

(E)-3β-(2-(1-Pyrrolidinyl)ethoxy)-17β-semicarbazonomethyl-5β-androstane- 14β-ol (I-as)

The title compound (I-as) (0.38 g) was obtained as a white solid starting from 3β-(2-(1-pyrrolidinyl)ethoxy)-17β-(2-(1,3-dioxolanyl))-5β-androstane- 14β-ol (0.80 g) (Prepn. 3) and semicarbazide hydrochloride following the procedure described in Ex. 14.

¹H-NMR (300 MHz, DMSO-d₆, ppm from TMS): 0.76 (3H, s); 0.85 (3H, s); 2.18 (1H, m); 2.44 (4H, m); 2.52 (2H, t); 3.39 (2H, m); 3.55 (1H, m); 3.96 (1H, s); 6.00 (2H, bb); 7.26 (1H, d); 9.65 (1H, s).

EXAMPLE 20

(E)-3β-(3-(1-Pyrrolidinyl)propoxy)-17β-semicarbazonomethyl- 5β-androstane-14β-ol (I-at)

The title compound (I-at) (0.38 g) was obtained as a white solid starting from 3β-(3-(1-pyrrolidinyl)propoxy)-17β-(2-(1,3-dioxolanyl))-5β-androstane- 14β-ol (0.80 g) (Prepn. 4) and semicarbazide hydrochloride following the procedure described in Ex. 14.

¹H-NMR (300 MHz, DMSO-d₆, ppm from TMS): 0.76 (3H, s); 0.85 (3H, s); 2.20 (1H, m); 2.45 (6H, m); 3.30 (2H, m); 3.52 (1H, m); 3.90 (1H, s); 6.00 (2H, bb); 7.24 (1H, d); 9.45 (1H, s).

EXAMPLE 21

(E)-3β-(3-Aminopropoxy)-17β(2-imidazolin-2-yl) hydrazonomethyl- 5β-androstane-14β-ol (I-au)

The title compound (I-au) (0.42 g) was obtained as a white solid starting from 3β-(3-aminopropoxy)-17β-(2-(1,3-dioxolanyl))-5β-androstane- 14β-ol (0.90 g) (Prepn. 1)and 2-hydrazino-2-imidazoline hydrobromide (see Ex. 3) using the same procedure described in Ex. 12.

¹H-NMR (300 MHz, DMSO-d₆, ppm from TMS): 0.90 (3H, s); 0.98 (3H, s); 2.40 (1H, m); 2.58 (2H, t); 3.30–3.50 (7H, m); 4.05 (1H, s); 4.15 (1H, d); 7.58 (1H, d); 7.50–9.00 (3H, bb).

EXAMPLE 22

(E)-3β-(2-Aminoethoxy)-17β-(2-imidazolin-2-yl) hydrazonomethyl- 5α-androstane-14β-ol (I-av)

The title compound (I-av) (0.30 g) was obtained as a white solid starting from 3β-(2-aminoethoxy)-17β-(2-(1,3-dioxolanyl))-5β-androstane- 14β-ol (0.80 g) (Prepn. 2) and 2-hydrazino-2-imidazoline hydrobromide using the same procedure described in Ex. 12.

¹H-NMR (300 MHz, DMSO-d₆, ppm from TMS): 0.90 (3H, s); 1.00 (3H, s); 2.40 (1H, m); 2.60 (2H, t); 3.30–3.50 (6H, m); 3.60 (1H, m); 4.00 (1H, s); 4.10 (1H, d); 7.60 (1H, d); 7.50–9.00 (3H, bb).

EXAMPLE 23

(E)-3β-(2-(1-Pyrrolidinyl)ethoxy)-17β-(2-imidazolin-2-yl)hydrazonomethyl-5β-androstane-14β-ol (I-aw)

The title compound (I-aw) (0.22 g) was obtained as a white solid starting from 3β-(2-(1-pyrrolidinyl)ethoxy)-17β-(2-(1,3-dioxolanyl))-5β-androstane- 14β-ol (0.75 g) (Prepn. 3) and 2-hydrazino-2-imidazoline hydrobromide using the same procedure described in Ex. 14.

¹H-NMR (300 MHz, DMSO-d₆, ppm from TMS): 0.78 (3H, s); 0.87 (3H, s); 2.20–2.35 (1H, m); 2.45 (4H, m); 2.53 (2H, t); 3.30–3.50 (6H, m); 3.55 (1H, m); 4.05 (1H, s); 5.50–6.50 (2H, bb); 7.60 (1H, d).

EXAMPLE 24

(E)-3β-(3-(1-pyrrolidinyl)propoxy)-17β-(2-imidazolin-2-yl)hydrazonomethyl-5β-androstane-14β-ol (I-ax)

The title compound (I-ax) (0.45 g) was obtained as a white solid stag from 3β-(3-(1-pyrrolidinyl)propoxy)-17β-(2-(1,3-dioxolanyl))-5β-androstane- 14β-ol (0.86 g) (Prepn. 4) and 2-hydrazino-2-imidazoline following the procedure described in Ex. 14.

¹H-NMR (300 MHz, DMSO-d₆, ppm from TMS): 0.77 (3H, s); 0.87 (3H, s); 2.20–2.35 (1H, m); 2.45 (6H, m); 3.30 (2H, m); 3.40–3.55 (5H, m); 3.90 (1H, s); 6.20 (2H, bb); 6.45 (1H, s); 7.22 (1H, d).

EXAMPLE 25

(E)-3β-(3-Aminopropoxy)-17β-(2-imidazolyl)
hydrazonomethyl- 5β-androstane-14β-ol (I-ay)

The title compound (I-ay) (0.47 g) was obtained as a white solid starting from 3β-(3-aminopropoxy)-17β-(2-(1, 3-dioxolanyl))-5β-androstane- 14β-ol (0.85 g) (Prepn. 1) and 2-hydrazinoimidazole (see Ex. 2) using the same procedure described in Ex. 12.

$^1$H-NMR (300 MHz, CDCl$_3$, ppm from TMS): 0.78 (3H, s); 0.89 (3H, s); 2.20–2.35 (1H, m); 2.58 (2H, t); 3.35 (2H, m); 3.52 (1H, m); 4.05 (1H, s); 4.15 (1H, d); 6.90 (2H, s).

EXAMPLE 26

(E)-3β-(3-Aminopropoxy)-17β-(1-methyl-2-
imidazolin-2-yl)-hydrazonomethyl-
5β-androstane-14β-ol (I-az)

The title compound (I-az) (0.32 g) was obtained as a white solid starting from 3β-(3-aminopropoxy)-17β-(2-(1,3-dioxolanyl))-5β-androstane- 14β-ol (0.77 g) (Prepn. 1)and 1-methyl-2-hydrazino-2-imidazoline hydroiodide (see Ex. 3) using the same procedure described in Ex. 12.

$^1$H-NMR (300 MHz, DMSO-d$_6$, ppm from TMS): 0.79 (3H, s); 0.89 (3H, s); 2.20–2.30 (1H, m); 2.56 (2H, t); 2.65 (3H, s); 3.22 (4H, s); 3.35 (2H, m); 3.54 (1H, m); 4.13 (1H, s); 7.54 (1H, d); 6.50 (1H, bb).

EXAMPLE 27

(E)-3β-(2-(1-Pyrrolidinyl)ethoxy)-17β-
(1-methyl-2-imidazolin-2
-yl)hydrazonomethyl-5β-androstane-14β-ol (I-ba)

The title compound (I-ha) (0.25 g) was obtained as a white solid starting from 3β-(2-(1-pyrrolidinyl)ethoxy)-17β-(2-(1,3-dioxolanyl))-5β-androstane- 14β-ol (0.70 g) (Prepn. 3) and 2-hydrazinoimidazoline hydrobromide using the same procedure described in Ex. 14.

$^1$H-NMR (300 MHz, DMSO-d$_6$, ppm from TMS): 0.76 (3H, s); 0.85 (3H, s); 2.20–2.30 (1H, m); 2.44 (4H, m); 2.52 (2H, t); 2.65 (3H, s); 3.22 (4H, s); 3.40 (2H, m); 3.53 (1H, m); 4.02 (1H, s); 5.50–6.50 (2H, bb); 7.58 (1H, d).

EXAMPLE 28

(E)-3β-(3-Aminopropoxy)-17β-(5-oxo-
2-imidazolin-2-yl)hydrazonomethyl-
5β-androstane-14β-ol (I-bb)

The title compound (I-bb) (0.40 g) was obtained as a white solid starting from 3β-(3-aminopropoxy)-17β-(2-(1, 3-dioxolanyl))-5β-androstane- 14β-ol (0.80 g) (Prepn. 1) and 5-oxo-2-hydrazinoimidazoline (see Ex. 4) using the same procedure described in Ex. 12.

$^1$H-NMR (300 MHz, DMSO-d$_6$, ppm from TMS): 0.75 (3H, s); 0.85 (3H, s); 2.20–2.30 (1H, m); 2.60 (2H, t); 3.35 (2H, m); 3.50 (1H, m); 3.75 (1H, d); 3.95 (1H, d); 4.05 (1H, s); 7.61 (1H, d); 8.00 (1H, bb).

EXAMPLE 29

(E)-3β-(2-(1-Pyrrolidinyl)ethoxy)-17β-(5-oxo-
2-imidazolin-2-yl)hydrazonomethyl-
5β-androstane-14β-ol (I-bc)

The title compound (I-bc) (0.32 g) was obtained as a white solid starting from 3β-(2-(1-pyrrolidinyl)ethoxy)-17β-(2-(1,3-dioxolanyl))-5β-androstane- 14β-ol (0.75 g) (Prepn. 3) and 2-hydrazinoimidazoline hydrobromide following the procedure described in Ex. 14.

$^1$H-NMR (300 MHz, DMSO-d$_6$, ppm from TMS): 0.79 (3H, s); 0.88 (3H, s); 2.20–2.30 (1H, m); 2.60 (2H, t); 3.33 (2H, m); 3.51 (1H, m); 3.75 (1H, d); 3.95 (1H0 d); 4.05 (1H, s); 7.60 (1H, d); 8.00 (1H, bb).

EXAMPLE 30

(E)-3β-(3-Aminopropoxy)-17β-(1,4,5,6-tetrahydro-2
-pyrimidinyl)hydrazonomethyl-5β-androstane-14β-ol
(I-bd)

The title compound (I-bd) (0.38 g) was obtained as a white solid starting from 3β-(3-aminopropoxy)-17β-(2-(1, 3-dioxolanyl))-5β-androstane- 14β-ol (0.88 g) (Prepn. 1) and 2-hydrazino-1,4,5,6-tetrahydro- 2-pyrimidine hydroiodide (see Ex. 5)using the same procedure described in Ex. 12.

$^1$H-NMR (300 MHz, DMSO-d$_6$, ppm from TMS): 0.77 (3H, s); 0.88 (3H, s); 2.25–2.35 (1H, m); 2.56 (2H, t); 3.32 (2H, m); 3.15 (4H, t); 3.53 (1H, m); 4.10 (1H, s); 7.55 (1H, d).

EXAMPLE 31

(E)-3β-(3-Aminopropoxy)-17β-(3-
phenylguanidino)iminomethyl-
5β-androstane-14β-ol (I-be)

The title compound (I-be) (0.27 g) was obtained as a white solid starting from 3β-(3-aminopropoxy)-17β-(2-(1, 3-dioxolanyl))-5β-androstane- 14β-ol (0.75 g) (Prepn. 1) and 1-amino-3-phenylguanidine hydroiodide following the procedure described in Ex. 12.

$^1$H-NMR (300 MHz, DMSO-d$_6$, ppm from TMS): 0.81 (3H, s); 0.89 (3H, s); 2.33 (1H, m); 2.56 (2H, t); 3.35 (2H, m); 3.53 (1H, m); 3.95 (1H s); 6.80 (1H, m); 7.20 (2H, m); 7.50 (2H, m); 7.61 (1H, d); 8.05 (1H, bb).

EXAMPLE 32

(E)-3β-(2-(1-Pyrrolidinyl)ethoxy)-17β-
(3-phenylguanidino)iminomethyl-
5β-androstane-14β-ol (I-bf)

The title compound (I-bf) (0.35 g) was obtained as a white solid starting from 3β-(2-(1-pyrrolidinyl)ethoxy)-17β-(2-(1, 3-dioxolanyl))-5β-androstane- 14β-ol (0.85 g) (Prepn. 3) and 1-amino-3-phenylguanidine hydroiodide using the same procedure described in Ex. 14.

$^1$H-NMR (300 MHz, DMSO-d$_6$, ppm from TMS): 0.82 (3H, s); 0.87 (3H, s); 2.36 (1H, m); 2.45 (4H, m); 2.53 (2H, t); 3.40 (2H, m); 3.54 (1H m); 4.12 (1H, s); 6.81 (1H, m); 7.22 (2H, m); 7.47 (2H, m); 7.60 (1H, d); 8.10 (1H, bb).

EXAMPLE 33

(E)-3β-(3-Aminopropoxy)-17β-
dimethylhydrazonomethyl-5β-androstane- 14β-ol,
(I-bg)

The title compound (I-bg) (0.30 g) was obtained as a white solid starting from 3β-(3-aminopropoxy)-17β-(2-(1, 3-dioxolanyl))-5β-androstane- 14β-ol (0.85 g) (Prepn. 1) and N,N-dimethylhydrazine using the same procedure described in Ex. 12.

$^1$H-NMR (300 MHz, DMSO-$d_6$, ppm from TMS): 0.74 (3H, s); 0.86 (3H, s); 2.15–2.25 (1H, m); 2.54 (6H, s); 2.58 (2H, t); 3.34 (2H, m); 3.53 (1H, m); 3.91 (1H, s); 6.76 (1H, d).

EXAMPLE 34

(E)-3β-(2-(1-Pyrrolidinyl)ethoxy)-17β-
dimethylhydrazonomethyl- 5β-androstane-14β-ol
(I-bh)

The title compound (I-bh) (0.30 g) was obtained as a white solid starting from 3β-(2-(1-pyrrolidinyl)ethoxy)-17β-(2-(1,3-dioxolanyl))-5β-androstane- 14β-ol (0.90 g) (Prepn. 3) and N,N-dimethylhydrazine using the same procedure described in Ex. 14.

$^1$H-NMR (300 MHz, DMSO-$d_6$, ppm from TMS): 0.73 (3H, s); 0.86 (3H, s); 2.15–2.25 (1H, m); 2.45 (4H, m); 2.51 (6H, s); 2.54 (2H, t); 3.39 (2H, m); 3.55 (1H, m); 3.94 (1H, s); 6.75 (1H, d).

EXAMPLE 35

3-[(ZE)-Guanidinoimino]-17β-[(E)-
guanidinoiminomethyl]-5β-androstane- 14β-ol (I-bi)

To a solution of 0.13 g of aminoguanidine hydrogencarbonate, 2.00 g of sodium acetate in 25 ml of 0.2M acetic acid a solution of 0.30 g 3-oxo-14β-hydroxy-5β-androstane-17β-carboxaldehyde (Prepn. 5) in 40 ml of dioxane was added dropwise. After 2 hrs the mixture was evaporated to dryness under reduced pressure and the crude product was extracted three times with iso-propanol. Evaporation of the solvent gave 0.30 g of (E)-3-oxo-17β-guanidinoiminomethyl-5β-androstane- 14β-ol acetate as a white foam.

$^1$H-NMR (300 MHz, DMSO-$d_6$, ppm from TMS): 0.80 (3H, s); 0.92 (3H, s); 1.82 (3H, s); 2.30 (1H, m); 2.70 (1H, m); 7.53 (1H, d).

To a refluxing solution of 0.080g of aminoguanidine hydrogencarbonate in 12 ml of 0.1M sodium hydroxide and 4 ml of ethanol a solution of 0.28 g of (E)-3-oxo-17β-guanidinoiminomethyl-5β-androstane- 14β-ol acetate in 4 ml of ethanol was added dropwise. After 2 hrs at reflux, the solution was evaporated to dryness under reduced pressure. The crude product was ground with water to give 0.12 mg of the title compound (I-bi) as a white solid.

$^1$H-NMR (300 MHz, DMSO-$d_6$, ppm from TMS): 0.76 (3H, s); 0.85 (3H, s); 2.27 (1H, m); 3.96 (1H, s); 5.00–6.00 (8H, bb); 7.43 (1H, d).

EXAMPLE 36

3-[(ZE)-(2-Imidazolin-2-yl)hydrazono]-17β-[(E)-
[2-imidazolin-2-yl)hydrazonomethyl]-
5β-androstane-14β-ol (I-bj)

The title compound (I-bj) (0.19 g) was obtained as a white solid starting from 3-oxo-14β-hydroxy-5β-androstane-17β-carboxaldehyde (0.50 g) (Prepn. 5) and 2-hydrazino-2-imidazoline hydrobromide using the same procedure described in Ex. 35.

$^1$H-NMR (300 MHz, DMSO-$d_6$, ppm from TMS): 0.77 (3H, s); 0.86 (3H, s); 2.25–2.35 (1H, m); 3.25–3.45 (8H, m); 7.45 (1H, s).

EXAMPLE 37

(E)-20-Guanidinoimino-5β-pregnane-3β,14β-diol
(I-bk)

A mixture of 1.00 g of 3β,14β-dihydroxy-5β-pregnane-20-one (Templeton J. F. et al., *J. Chem. Soc., Perkin Trans.* 1, 1991, 823), 1.20 g of aminoguanidine hydrogencarbonate in 40 ml of dioxane and 10 ml of water acidified at pH 2.5 with 0.01M hydrochloric acid was stirred at room temperature for 3 days. The precipitate was collected by filtration and purified by flash-chromatography (SiO$_2$) using chloroform/methanol/28% ammonium hydroxide 78/20/2; the fractions containing the title compound were collected and evaporated to dryness. The crude product was ground with ethanol to give 0.40 g of the title compound (I-bk) as a white solid.

$^1$H-NMR (300 MHz, CD$_3$OD, ppm from TMS): 0.90 (3H, s); 0.97 (3H, s); 2.02 (3H, s); 2.62 (1H, t); 4.05 (1H, m).

EXAMPLE 38

(E)-17β-Guanidinoiminomethyl-5β-
androstane-3β,14β,17α-triol (I-bl)

To a refluxing solution of 0.10 g of aminoguanidine hydrogencarbonate in 7.5 ml of 0.1M sodium hydroxide a solution of 0.24 g of 3β-acetoxy-14β,17α-dihydroxy-5β-androstane-17β-carboxaldehyde (Prepn. 6) in 20 ml of dioxane was added dropwise. After 2 hrs at reflux, 0.75 ml of 1M sodium hydroxide were added and the solution was refluxed for 4 hrs. The mixture was evaporated to dryness under reduced pressure. The crude product was ground with ethanol/water and then with ethanol/diethyl ether to give 0.15 g of the title compound (I-bl) as a white solid.

$^1$H-NMR (300 MHz, DMSO-$d_6$, ppm from TMS): 0.62 (3H, s); 0.88 (3H, s); 3.88 (1H, m); 3.92 (1H, s); 4.18 (1H, m); 4.60 (1H, s); 4.98 (2H, bb); 5.78 (2H, bb); 7.76 (1H, s).

EXAMPLE 39

(E)-17β-Semicarbazonomethyl-5β-
androstane-3β,14β,17α-triol (I-bm)

The title compound (I-bm) (0.25 g) was obtained as a white solid starting from 3β-acetoxy-14β,17α-dihydroxy-5β-androstane-17β-carboxaldehyde (0.60 g) (Prepn. 6) and semicarbazide hydrochloride using the same procedure described in Ex. 38.

$^1$H-NMR (300 MHz, CDCl$_3$, ppm from TMS): 0.85 (3H, s); 0.98 (3H, s); 7.43 (1H, s).

EXAMPLE 40

(E)-17β-(2-Imidazolin-2-yl)hydrazonomethyl-
5β-androstane- 3β,14β,17α-triol (I-bn)

A solution of 0.44 g of 3β-acetoxy-14β,17α-dihydroxy-5β-androstane- 17β-carboxaldehyde (Prepn. 6) and 0.26 g of 2-hydrazino- 2-imidazoline hydrobromide in 50 ml of dioxane and 2 ml of water was stirred for 18 hrs. The solution was evaporated to dryness under reduced pressure and the residue was ground with water to give 0.52 g of (E)-17β-(2-imidazolin-2-yl)hydrazonomethyl-5β-androstane-3β-acetoxy- 14β,17α-diol hydrobromide.

$^1$H-NMR (300 MHz, DMSO-d$_6$, ppm from TMS): 0.65 (3H, s); 0.88 (3H, s); 1.98 (3H, s); 3.70 (4H, s); 4.22 (1H, s); 4.55 (1H, s); 4.95 (1H, m); 8.04 (1H, s).

A solution of 0.46 g of (E)-17β-(2-imidazolin-2 -yl)hydrazonomethyl-5β-androstane-3β-acetoxy-14β,17α-diol and 17 ml of 0.1M sodium hydroxide in 16 ml of methanol was stirred for 24 hrs. After evaporation of the methanol under reduced pressure the precipitate was filtered and washed with water to give 0.30 g of the title compound (I-bn) as a white solid.

$^1$H-NMR (300 MHz, DMSO-d6,-ppm from TMS): 0.60 (3H, s); 0.85 (3H, s); 3.25–3.45 (4H, m); 3.87 (1H, s); 3.94 (1H, s); 4.18 (1H, bs); 4.62 (1H, s); 5.95 (1H, s); 6.90 (1H, s); 7.75 (1H, s).

EXAMPLE 41

(E)-17-(2-Imidazolin-2-yl)hydrazono-5β-androstane-3β,14β-diol (I-bo)

A mixture of 0.60 g of 3β,14β-dihydroxy-5β-androstane-17-one (Lindig C., *J. Prakt. Chem.*, 1983, 325, 587), 1.00 g of 2-hydrazino-2 -imidazoline hydrobromide and 1.50 ml of triethylamine in 50 ml of ethanol and 50 ml of water was stirred at reflux for 2 days. After cooling the mixture was added with 1N sodium hydroxide until pH 12.5 was reached. The mixture was evaporated under reduced pressure and the residue was purified by flash-chromatography (SiO$_2$) using chloroform/methanol/28% ammonium hydroxide 88/20/2 as eluant; the fractions containing the title compound were collected and evaporated to dryness. The residue was ground with ethanol/diethyl ether to give 0.43 g of the title compound (I-bo) as a white solid.

$^1$H-NMR (300 MHz, DMSO-d$_6$, ppm from TMS): 0.88 (3H, s); 1.00 (3H, s); 2.25–2.40 (2H, m); 3.25–3.45 (4H, m); 3.85 (1H, s); 3.89 (1H, bs); 4.18 (1H, d); 5.90 (1H, s); 6.95 (1H, s).

EXAMPLE 42

(E)-17-(1,4,5,6-Tetrahydro-2-pyrimidinyl) hydrazono-5β-androstane- 3β,14β-diol (I-bp)

The title compound (I-bp) (0.39 g) was obtained as a white solid starting from 3β,14β-dihydroxy-5β-androstane-17-one (0.60 g) (Lindig C., *J. Prakt. Chem.*, 1983, 325, 587) and 2-hydrazino-1,4,5,6 -tetrahydro-2-pyrimidine hydroiodide (prepared from 2-methylthio- 1,4,5,6-tetrahydro-2-pyrimidine hydroiodide and hydrazine following the procedure described in Houben-Weil, Metoden der Organischen Chemie, Band VIII, page 183) using the same procedure described in Ex. 41.

$^1$H-NMR (300 MHz, DMSO-d$_6$, ppm from TMS): 0.88 (3H, s); 1.00 (3H, s); 2.25–2.40 (2H, m); 3.20 (4H, t); 3.86 (1H, bs); 3.90 (1H, s); 4.16 (1H, d); 5.80 (1H, s); 6.85 (1H, s).

PREPARATION 1

3β-(3-Aminopropoxy)-17β-(2-(1,3-dioxolanyl)-5β-androstan- 14β-ol (II-a)

A solution of 6.00 g of 3β,14β-dihydroxy-5β-androstane- 17β-carboxaldehyde (Boutagy J. and Thomas R., *Aust. J. Chem*, 1971, 24, 2723), 0.80 g of oxalic acid and 10.0 ml of ethylene glycol in 120 ml of acetonitrile was stirred at room temperature for 24 hrs. After alcalinization with acqueous sodium hydrogencarbonate the mixture was extracted with ethyl acetate; the organic layer was dried over anhydrous sodium sulfate and evaporated to dryness under reduced pressure to give 6.50 g of 17β-(2-(1,3-dioxolanyl))-5β-androstane- 3β,14β-diol as a dense oil.

$^1$H-NMR (300 MHz, CDCl$_3$, ppm from TMS): 0.98 (3H,s); 1.05 (3H, s); 3.80–4.20 (5H, m); 4.98 (1H, d).

To a solution of 6.00 g of 17β-(2-(1,3-dioxolanyl))-5β-androstan- 3β,14β-diol in 50 ml of dry tetrahydrofuran, 4.40 g of sodium hydride (60% dispersion in mineral oil) were added under nitrogen atmosphere at room temperature and the resulting mixture was stirred at reflux temperature for 6 hrs; 14.0 g of allyl bromide were added and the reflux continued for further 20 hrs. The mixture was quenched with water and the organic solvent was distilled under reduced pressure. The residue was extracted with ethyl acetate; the organic solution was dried over anhydrous sodium sulfate and evaporated to dryness under reduced pressure. The residue was purified by flash-chromatography (SiO$_2$) using n-hexane/ethyl acetate 80/20 as eluant to give 5.88 g of 3β-prop-( 2-en)oxy-17β-(2-(1,3-dioxolanyl))-5β-androstan-14β-ol as a white solid.

$^1$H-NMR (300 MHz, CDCl$_3$, ppm from TMS): 0.97 (3H, s); 1.04 (3H, s); 2.74 (1H, dd); 3.69 (1H, bs); 3.80–4.20 (6H, m); 4.99 (1H, d); 5.12–5.18 (1H, m); 5.22–5.32 (1H, m); 5.87–6.01 (1H, m).

To a solution of 1.70 g of 9-borabicyclo[3.3.1]nonane in 350 ml of dry tetrahydrofuran, 5.00 g of 3β-prop-(2-en)oxy-17β-(2-(1,3 -dioxolanyl))-5β-androstan-14β-ol in 100 ml of tetrahydrofuran were added under nitrogen atmosphere, at room temperature. The solution was stirred for 6 hrs then 7.5 ml of ethanol, 2.5 ml of 6N sodium hydroxide and 5 ml of hydrogen peroxide 30% were added. The mixture was stirred at 50° C. for 1 hr, quenched with a solution of 7.6 g of potassium carbonate in 200 ml of water and the organic solvent distilled under reduced pressure. The residue was extracted with methylene chloride, the organic solution was dried over anhydrous sodium sulfate and evaporated to dryness under reduced pressure. The residue was purified by flash-chromatography (SiO$_2$) using n-hexane/ethyl acetate 70/30 as eluant to give 4.05 g of 3β-(3 -hydroxypropoxy)-17β-(2-(1,3-dioxolanyl))5β-androstan-14β-ol as a white amorphous solid.

$^1$H-NMR (300 MHz, CDCl$_3$, ppm from TMS): 0.96 (3H, s); 1.05 (3H, s); 3.57–3.67 (3H, m); 3.80–4.20 (6H, m); 4.98 (1H, d).

A solution of 0.29 ml of diethyl azodicarboxylate was added dropwise, under nitrogen, to a solution of 3.75 g of 3β-(2 -hydroxypropoxy)-17β-(2-(1,3-dioxolanyl))-5β-androstan-14β-ol, 1.24 g of phthalimide and 2.50 g of triphenylphosphine in 35 ml of tetrahydrofuran at room temperature. After 2 hrs the solvent was removed in vacuo, the crude product was dried over anhydrous sodium sulfate and evaporated to dryness under reduced pressure. The crude product was purified by flash-chromatography (SiO$_2$) using n-hexane/ethyl acetate 80/20 to give 3.50 g of 3β-(3 -phthalimidopropoxy)-17β-(2-(1,3-dioxolanyl))-5β-androstan-14β-ol.

$^1$H-NMR (300 MHz, CDCl$_3$, ppm from TMS): 0.87 (3H, s); 1.03 (3H, s); 3.38–3.50 (2H, m); 3.52 (1H, m); 3.80–4.20 (6H, m); 4.99 (1H, d); 7.68–7.75 (2H, m); 7.80–7.90 (2H, m).

To a solution of 3.00 g of 3β-(3-phthalimidopropoxy)-17β-(2-(1,3 -dioxolanyl))-5β-androstan-14β-ol in 300 ml of ethanol (96%) 1.20 g of hydrazine hydrate were added at room temperature. The mixture was kept at reflux for 4 hrs, then 10 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography ($SiO_2$) using methylene chloride/methanol 90/10 as eluant to give 2.00 g of the title compound (II-a) as a white solid.

$^1$H-NMR: (300 MHz, $CDCl_3$, ppm from TMS): 0.95 (3H, s); 1.05 (3H, s); 2.60–2.80 (2H, m); 3.30–3.40 (2H, m); 3.58 (1H, bs); 3.80–4.20 (4H, m); 4.98 (1H, d).

PREPARATION 2

3β-(2-Aminoethoxy)-17β-(2-(1,3-dioxolanyl))-5β-androstan-14β-ol (II-b)

To a suspension of 5.5 g of NaH (60 % dispersion in mineral oil) in 400 ml of dry tetrahydrofuran 7.0 g of 17β-(2-(1,3-dioxolanyl))-5β-androstan- 3β,14β-diol (see Prepn. 1) were added at room temperature in a nitrogen atmosphere. The mixture was kept at reflux for 6 hrs, then 26 ml of bromoacetaldehyde diethylacetal were added and the suspension was stirred at reflux for 4 hrs. After cooling at room temperature 50 ml of water were added cautiously, and tetrahydrofuran was distilled under reduced pressure. The residue was extracted with methylene chloride, the organic layer was dried over anhydrous sodium sulfate and evaporated to dryness under reduced pressure. The crude product was purified by flash-chromatography ($SiO_2$) using n-hexane/ethyl acetate 80/20 as eluant to give 6.9 g of 3β-(2,2 -diethoxyethoxy)-17β-(2-(1,3-dioxolanyl))-5β-androstan-14β-ol, as a dense oil.

$^1$H NMR (300 MHz, $CDCl_3$, ppm from TMS): 0.97 (3H, s); 1.03 (3H, s); 1.24 (6H, t); 3.47–3.50 (2H, m); 3.50–3.80 (5H, m); 3.80–4.20 (4H, m); 4.62 (1H, t); 4.99 (1H, d).

A solution of 6.80 g of 3β-(2,2-diethoxyethoxy)-17β-(2-(1,3 -dioxolanyl))-5β-androstan-14β-ol, in 550 ml of dioxane and 430 ml of a saturated aqueous solution of tartaric acid was heated at 70° C. for two hrs in a nitrogen atmosphere. After cooling at room temperature, 200 ml of water were added and the mixture was extracted with methylene chloride. The organic layer was washed with water, dried over anhydrous sodium sulfate and evaporated to dryness under reduced pressure. The crude product was purified by flash-chromatography ($SiO_2$) using as eluant n-hexane/ethyl acetate 70/30 to give 2.11 g of 3-β-formylmethoxy-17β-(2-(1,3-dioxolanyl))-5β-androstan-14β-ol as a white waxy solid.

$^1$H NMR: (300 MHz, $CDCl_3$, ppm from TMS): 0.97 (3H, s); 1.03 (3H, s); 3.70 (1H, bs); 3.80–4.20 (4H, m); 4.10 (2H, d); 4.97 (1H, d); 9.75 (1H, t).

To a solution of 2.00 g of 3-β-formylmethoxy-17β-(2-(1,3 -dioxolanyl))-5β-androstan-14β-ol in 200 ml of methanol, 0.60 g of sodium borohydride were added slowly at 0° C. After 30 min. the temperature of the mixture was left to rise to 25° C. After 2 hrs 40 ml of water were added, methanol was distilled under reduced pressure, and the residue was extracted with methylene chloride; the organic layer was washed with water, dried over sodium sulfate and evaporated to dryness under reduced pressure. The crude product was purified by flash-chromatography ($SiO_2$) using n-hexane/ethyl acetate 80/20 as eluant to give 1.70 g of 3β-(2-hydroxyethoxy)-17β-(2-(1,3-dioxolanyl))- 5β-androstan-14β-ol as a white solid.

$^1$H NMR (300 MHz, $CDCl_3$, ppm from TMS): 0.96 (3H, s); 1.04 (3H, s); 3.48 (2H, t); 3.63 (1H, bs); 3.70 (2H, t); 3.80–4.20 (4H, m); 4.98 (1H, d).

A solution of 0.60 ml of diethyl azodicarboxylate was added dropwise, under nitrogen, to a solution of 1.65 g of 3β-(2 -hydroxyethoxy)-17β-(2-(1,3-dioxolanyl))-5β-androstan-14β-ol, 0.60 g of phthalimide and 1.00 g of triphenylphosphine in 15 ml of tetrahydrofuran was stirred at room temperature. After 2 hrs the solvent was removed in vacuo, the crude product was dried over anhydrous sodium sulfate and evaporated to dryness under reduced pressure. The crude product was purified by flash-chromatography ($SiO_2$) using n-hexane/ethyl acetate 80/20 to give 1.65 g of 3β-(2 -phthalimidoethoxy)-17β-(2-(1,3-dioxolanyl))-5β-androstan-14β-ol.

$^1$H NMR (300 MHz, $CDCl_3$, ppm from TMS): 0.95 (3H, s); 1.05 (3H, s); 3.60–3.68 (3H, m); 3.80–4.20 (6H, m); 4.98 (1H, d); 7.70–7.75 (2H, m); 7.80–7.90 (2H, m).

To a solution of 1.50 g of 3β-(2-phthalimidoethoxy)-17β-(2-(1,3 -dioxolanyl))-5β-androstan-14β-ol in 90 ml of ethanol (96%) 0.50 ml of hydrazine hydrate were added at room temperature. The mixture was stirred at reflux for 4 hrs, then 20 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography ($SiO_2$) using methylene chloride/methanol 90/10 as eluant to give 0.75 g of the title compound (II-b) as a white solid.

$^1$H NMR: (300MHz, $CDCl_3$, ppm from TMS): 0.97 (3H, s); 1.03 (3H, s); 2.84 (2H, t); 3.41 (2H, m); 3.65 (1H, bs); 3.80–4.20 (4H, m); 4.98 (1H, d).

PREPARATION 3

3β-(2-(1-Pyrrolidinyl)ethoxy)-17β-(2-(1,3-dioxolanyl)1-5β-androstane- 14β-ol (II-c)

A mixture of 3.20 g of 17β-(2-(1,3-dioxolanyl))-5β-androstane- 3β,14β-diol (see Prepn. 1), 18.4 g of 1-(2-chloroethyl)pyrrolidine and 5.60 g of sodium hydride (55% dispersion in mineral oil) in 300 ml of dry tetrahydrofuran was refluxed for 12 hrs. After cooling, water was added and the mixture was extracted with ethyl acetate; the organic layer was dried over anhydrous sodium sulfate and evaporated to dryness under reduced pressure. The crude product was purified by flash-chromatography ($SiO_2$) using chloroform/methanol 95/5 as eluant; the fractions containing the title compound were collected and evaporated to give 2.55 g of the title compound (II-c) as a dense oil.

$^1$H-NMR: (300 MHz, $CDCl_3$, ppm from TMS): 0.93 (3H, s); 1.04 (3H, s); 2.05 (1H, m); 2.85 (6H, m); 3.63 (3H, m); 3.80–4.13 (4H, m); 4.99 (1H, d).

PREPARATION 4

3β-(3-(1-Pyrrolidinyl)propoxy)-17β-(2-(1,3-dioxolanyl))-5β-androstane-14β-ol (II-d)

The title compound (II-d) (2.70 g) was obtained as a dense oil starting from 3.20 g of 17β-(2-(1,3-dioxolanyl))-5β-androstane-3β,14β-diol (see Prepn. 1) and 20.0 g of 1-(3-chloropropyl)pyrrolidine using the same procedure described in Prepn. 3.

¹H-NMR (300 MHz, CDCl₃, ppm from TMS): 0.93 (3H, s); 1.04 (3H, s); 2.05 (1H, m); 2.55 (6H, m); 3.42 (2H, t); 3.62 (1H, m); 3.80–4.13 (4H, m); 4.99 (1H, d).

PREPARATION 5

3-Oxo-14β-hydroxy-5β-androstane-17β-carboxaldehyde (II-e)

To a suspension of 0.88 g of pyridinium dicromate in 2.2 ml of dichloromethane a solution of 0.50 g of 3β,14β-dihydroxy-5β-androstane- 17β-carboxaldehyde (Boutagy J. and Thomas R., *Aust. J. Chem.*, 1971, 24, 2723) in 2.5 ml of dichloromethane was added at room temperature. After 20 hrs the mixture was diluted with diethyl ether and filtered through celite; the filtrate was evaporated to dryness under reduced pressure. The crude product was purified by flash-chromatography (SiO₂) using n-hexane/ethyl acetate 6/4 as eluant; the fractions containing the title compound were collected and evaporated to give 0.30 g of the title compound (II-e) as a white foam.

¹H-NMR (300 MHz, CDCl₃, ppm from TMS): 1.02 (3H, s); 1.06 (3H, s); 2.25–2.40 (1H, m); 2.62 (2H, m); 9.72 (1H, d).

PREPARATION 6

3β-Acetoxy-14β,17α-dihydroxy-5β-androstane-17β-carboxaldehyde (II-f)

A mixture of 1.60 g of 3β-acetoxy-14β-hydroxy-5β-androstane- 17β-carboxaldehyde (Boutagy J. and Thomas R., *Aust. J. Chem.*, 1971, 24, 2723), 0.83 g of selenium dioxide and 1.20 ml of pyridine in 20 ml of dioxane was heated at 80° C. for 12 hrs. After cooling the mixture was filtered and the filtrate washed with acqueous sodium hydrogencarbonate and extracted with ethyl acetate. The organic layer was dried over anhydrous sodium sulfate and evaporated to dryness. The crude product was purified by flash-chromatography (SiO₂) using n-hexane/ethyl acetate 6/4 as eluant; the fractions containing the title compound were collected and evaporated to give 0.55 g of the title compound (II-f) as a white solid.

¹H-NMR (300 MHz, CDCl₃, ppm from TMS): 0.80 (3H, s); 0.99 (3H, s); 2.08 (3H, s); 3.69 (1H, s); 5.11 (1H, m); 9.98 (1H, s).

We claim:

1. A 17-Hydrazonomethyl- and 17-hydrazono-14β-hydroxy- 5β-androstane compound of the formula (I):

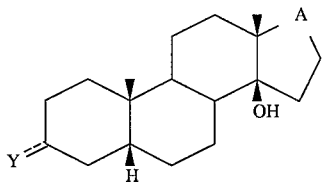

wherein:
the symbol --- represents a single or a double bond;
A represents

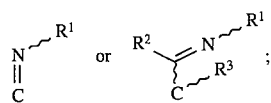

the symbol ∼∼∼ represents α or β configuration or a Z or E configuration; and when --- is a single bond, Y represents β-OR⁴;

when --- is a double bond, Y represents a N NHC(=N ∼∼∼R⁵)NR⁶R⁷ group;

R¹ represents NHC(=X)T or NR⁶R⁷;

X represents O, S or N ∼∼∼R⁵;

T represents NR⁶R⁷;

R² represents hydrogen or methyl;

R³ represents hydrogen or hydroxy;

R⁴ represents hydrogen, C2–C4 alkyl unsubstituted or substituted by NR⁹R¹⁰;

R⁵ represents hydrogen, methyl, C2–C4 alkyl, C2–C4 acryl or phenyl, where the C2–C4 alkyl, C2–C4 acyl are unsubstituted or substituted by NR⁹R¹⁰; and R⁵, R⁶, R⁷ taken two by two form, together with the heteroatoms they are linked to and where possible, a five-membered heteromonocyclic ring; or the pharmaceutically acceptable salts thereof.

2. The compound according to claim 1, which is selected from the group consisting of:
(E)-17β-(2-imidazolin-2-yl)hydrazonomethyl-5β-androstane- 3β,14β-diol,
(E)-17β-(2-imidazolyl)hydrazonomethyl-5β-androstane-3β,14β-diol,
(E)-17β-(1-methyl-2-imidazolin-2-yl)hydrazonomethyl-5β-androstane- 3β,14β-diol,
(E)-17β-(5-oxo-2-imidazolin-2-yl)hydrazonomethyl-5β-androstane- 3β,14β-diol,
(E)-3β-(3-aminopropoxy)-17β-(2-imidazolin-2-yl)hydrazonomethyl- 5β-androstane-14β-ol,
(E)-3β-(3-aminopropoxy)-17β-(2-imidazolyl)hydrazonomethyl- 5β-androstane-14β-ol,
(E)-3β-(3-aminopropoxy)-17β-(1-methyl-2-imidazolin-2-yl)hydrazonomethyl- 5β-androstane-14β-ol,
(E)-3β-(3-aminopropoxy)-17β-(5-oxo-2-imidazolin-2-yl) hydrazonomethyl- 5β-androstane-14β-ol,
3-((Z, E)-(2-imidazolin-2-yl)hydrazono)-17β-((E)-(2-imidazolin- 2-yl)hydrazono)methyl-5β-androstane-14β-ol,
(E)-20-(2-imidazolin-2-yl)hydrazono-5β-pregnane-3β,14β-diol,
(E)-17β-(2-imidazolin-2-yl)hydrazonomethyl-5β-androstane- 3β,14β,17α-triol,
(E)-17β-(2-imidazolyl)hydrazonomethyl-5β-androstane-3β,14β,17α-triol,
(E)-17β-(1-methyl-2-imidazolin-2-yl)hydrazonomethyl-5β-androstane- 3β,14β,17α-triol,
(E)-17β-(5-oxo-2-imidazolin-2-yl)hydrazonomethyl-5β-androstane- 3β,14β,17α-triol,
(E)-3β-(3-aminopropoxy)-17β-(2-imidazolin-2-yl)hydrazono-methyl- 5β-androstane-14β,17α-diol,
(E)-3β-(3-aminopropoxy)-17β-(2-imidazolyl)hydrazonomethyl- 5β-androstane-14β,17α-diol,
(E)-3β-(3-aminopropoxy)-17β-(1-methyl-2-imidazolin-2-yl)hydrazonomethyl- 5β-androstane-14β,17α-diol,
(E)-3β-(3-aminopropoxy)-17β-(5-oxo-2-imidazolin-2-yl) hydrazonomethyl- 5β-androstane-14β,17α-diol,
3-((Z,E)-(2-imidazolin-2-yl)hydrazono)-17β-((E)-(2 -imidazolin-2-yl)hydrazono)methyl-5β-androstane-14β,17α-diol,
(E)-17-(2-imidazolin-2-yl)hydrazono-5β-androstane-3β, 14β-diol, and
(E)-3β-(3-aminopropoxy)-17-(2-imidazolin-2-yl)hydrazono- 5β-androstane-14β-ol,
and when the (E) isomers are present the corresponding (Z) isomers are also present:

and when the 3β-(3-aminopropoxy) substituents are present also the corresponding 3β-(3-dimethylaminopropoxy), 3β-(3-diethylaminopropoxy), 3β-(3-(1-pyrrolidinyl)propoxy), 3β-(2-aminoethoxy), 3β-(2-dimethylaminoethoxy), 3β-(2-diethylaminoethoxy) and 3β-(2-(1-pyrrolidinyl)ethoxy) compounds.

3. The compound according to claim 1, which is a steroisomer, Z or E isomer, tautomer, optical isomer or mixtures thereof.

4. The compound according to claim 1, wherein said pharmaceutically acceptable salt is a salt of hydrochloric, hydrobromic, sulfuric, phosphoric, fumaric, succinic, oxalic, malic, tartaric, maleic, citric, methanesulfonic or benzoic acid.

5. The compound according to claim 1, wherein said $R^4$ is selected from the group consisting of hydrogen, 2-aminoethyl, 3-aminoethyl, 2-dimethylaminoethyl, 3-dimethylaminopropyl, 2-diethylaminoethyl, 3-diethylaminopropyl, 2-(1-pyrrolidinyl) ethyl and 3-(1-pyrrolidinyl)-propyl.

6. The compound according to claim 1, wherein said $R^5$ is selected from the group consisting of hydrogen, methyl, 2-aminoethyl, 3-aminopropyl, 2-dimethylaminoethyl, 3-dimethylaminopropyl, 2-(1-pyrrolidinyl)ethyl, 3-(1-pyrrolidinyl)propyl, acetyl and phenyl.

7. The compound according to claim 1, wherein said $NR^9R^{10}$ group is selected from the group consisting of amino, methylamino, dimethylamino, ethylamino, diethylamino, iso-propylamino, pyrrolidinyl and morpholino.

8. The compound according to claim 1, wherein said $R^5$ and $R^6$ groups taken together with the heteroatam linked therewith form a ring selected from the group consisting of 2-imidazolin- 2-yl, 1-methyl-2-imidazolin-2-yl, 5-oxo-2-imidazoliln- 2-yl, 1-methyl-5-oxo-2-imidazolin-2-yl, 2-imidazolyl and 2-(1-methyl)imidazolyl.

9. A pharmaceutical composition, which comprises a compound of the formula (I) of claim 1, with a pharmaceutically acceptable carrier or diluent.

* * * * *